United States Patent [19]

Herrinton

[11] Patent Number: 5,510,537
[45] Date of Patent: Apr. 23, 1996

[54] PREPARATION OF ALPHA, BETA-UNSATURATED ENONES

[75] Inventor: Paul M. Herrinton, Kalamazoo, Mich.

[73] Assignee: The Upjohn Company, Kalamazoo, Mich.

[21] Appl. No.: 427,935

[22] Filed: Apr. 26, 1995

Related U.S. Application Data

[63] Continuation of Ser. No. 242,585, May 13, 1994, abandoned, which is a continuation of PCT/US93/10253, Dec. 2, 1992, which is a continuation of Ser. No. 924,288, Aug. 3, 1992, abandoned, which is a continuation-in-part of Ser. No. 805,507, Dec. 10, 1991, abandoned.

[51] Int. Cl.$^6$ .................................................. C07C 45/00
[52] U.S. Cl. ........................ 568/311; 568/385; 549/361
[58] Field of Search .................................. 568/403, 405, 568/311, 385; 549/361

[56] References Cited

U.S. PATENT DOCUMENTS

| | | | |
|---|---|---|---|
| 4,215,044 | 7/1980 | Middleton | 549/70 |
| 4,603,212 | 7/1986 | White | 549/361 |
| 4,908,451 | 3/1990 | Tanaka et al. | 546/267 |

FOREIGN PATENT DOCUMENTS

| | | | |
|---|---|---|---|
| 1340612 | 12/1973 | United Kingdom | 171/175 |

OTHER PUBLICATIONS

Holger et al., Journal of the American Chemical Society, vol. 107, No. 1, pp. 268–270 (1985).

Hosokawa et al., Chemistry Letters, No. 7, pp. 1081–1082 (1983).

D. R. White, et al., Tetrahedron Letters, vol. 30, No. 12, 1469–1472 (1989).

Rubottom et al. J. Org. Chem. 43(8) 1978 1599–1602.

Beckworth et al, J. Amer. Chem. Soc 1985 [1986] 108, 8230–8234.

Kharasch et al, J. Organ. Chem., 1953, 18, 322–327.

Kaneda et al, Tet. Let., 1981, 2595–2598.

*Primary Examiner*—Rebecca Cook
*Attorney, Agent, or Firm*—Donald L. Corneglio

[57] ABSTRACT

A process for oxidizing silyl enone ethers to alpha, beta-unsaturated enodes having the formulas

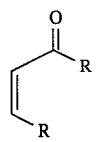

I

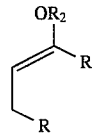

II which comprises reacting the appropriate silyl enone ether with a radical generated by the metal catalyst decomposition of a peroxide composition.

4 Claims, No Drawings

PREPARATION OF ALPHA, BETA-UNSATURATED ENONES

CROSS REFERENCE TO RELATED APPLICATIONS

This application is a continuation of U.S. Ser. No. 08/242,585, filed 13 May 1994 abandoned; which is a continuation of International Application No. PCT/US92/10253, filed 2 Dec. 1992; which is a continuation of U.S. Ser. No. 07/924,288, filed 3 Aug. 1992, abandoned; which is a continuation-in-part of U.S. Ser. No. 07/805,507, filed 10 Dec. 1991, abandoned.

FIELD OF THE INVENTION

This invention concerns a process of oxidizing silyl enol ethers to alpha, beta-unsaturated enones by means of radical intermediates. More specifically it relates to preparing enones that are intermediates for spectinomycin and its analogs. Spectinomycin and its analogs are known antibiotics and are described in U.S. Pat. No. 4,532,336.

INFORMATION DISCLOSURE

Hydroperoxides are known to decompose with metal catalyst to give radicals which can be used for abstraction of allyl hydrogen atom, A. L. J. Beckwith et al, *J. Amer. Chem, Soc.* 1985, 108, 8230–8234 and M. S. Kharasch et al, *J. Org. Chem,* 1953 18, 322–327. Oxidation of silyl enol ethers with metals and hydroperoxides has been reported to give diacids and ketoacids, K. Kaneda et al, *Tet. Let,* 1981, 2595– 2598.

SUMMARY OF THE INVENTION

The present invention provides:

A process for preparing an alpha, beta-unsaturated enone of Formula I

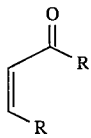

which comprises oxidizing a silyl enol ether of Formula II

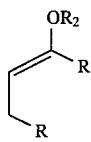

with a radical intermediate generated by metal catalyst decomposition of a peroxide in the presence of a solvent, wherein R is selected from the group consisting of ($C_1$–$C_8$) alkyl, phenyl, and substituted phenyl, or the two R groups together can form the residue of a ring system; and $R_2$ is selected from the group consisting of triethylsilyl, trimethylsilyl, triphenylsilyl and diphenylmethylsilyl; with the proviso that the peroxide used cannot be hydrogen peroxide.

A preferred embodiment of this invention is a process for preparing an alpha, beta-unsaturated enone of a spectinomycin analog of Formula III

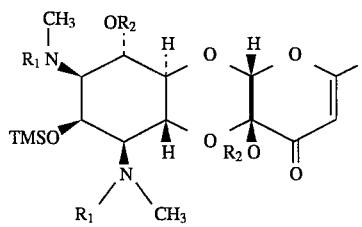

where TMSO is trimethylsilyl oxygen which comprises oxidizing a silyl enol ether of Formula IV

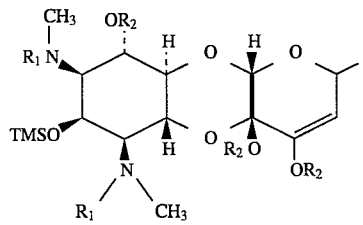

with a radical intermediate generated by the metal catalyst decomposition of a peroxide in the presence of a solvent wherein $R_1$ is selected from the group consisting of alkoxycarbonyl, and halogenated carbonyl, and $R_2$ is selected from the group consisting of triethylsilyl, trimethylsilyl, triphenylsilyl, and diphenylmethylsilyl.

DETAILED DESCRIPTION

In this process free radical intermediates are utilized to oxidize silyl enol ethers to alpha, beta-unsaturated enones. The radical intermediates are generated by the metal catalyst decomposition of peroxides.

The term ($C_1$–$C_8$) alkyl means methyl, ethyl, propyl, butyl, pentyl, hexyl, heptyl, octyl and isomeric forms thereof:

The terms alkoxycarbonyl, halogenareal carbonyl, and alkoxycarbonyl are terms described in the art, see U.S. Pat. No. 4,532,336.

The term residue of a ring system means any ring that has as part of its structure a silyl enol ether with a beta hydrogen.

The term "metal catalyst" means the salts of the various metals including hydrates thereof.

A large number of peroxides including di-t-butyl peroxide, decanoyl peroxide, benzoyl peroxide, lauroyl peroxide, cumene hydroperoxide, and t-butyl hydroperoxide can be used; but hydrogen peroxide cannot be used. The reaction can be catalyzed with metal catalyst including cuprous chloride, cupric chloride cuprous acetate, maganese acetate, nickel acetate, cesium chloride and chromium acetate. It is probable that any type of acetate would work with the exception of silver acetate. The amount of catalysts used is from about 0.5 to 10% with the preferred amount being about 3% based upon the amount of silyl enol ether present in the reaction.

The solvent is also important. The reaction works well with any halogenated solvent, dichloroethane, etc. or acetonitrile. While the acetonitrile gives the fastest reaction it also results in the loss of some silyl protecting groups. The preferred solvent is methylene chloride.

The water content of peroxide composition can be varied from 0 to 70%. The ratio of peroxide to enol ether in the reaction is 0.01 to 3 equivalents to 1 equivalent. The preferred ratio is about 1.5:1. The reaction is conducted at a temperature of −10° C. to 60° C.

EXAMPLE

[4a, 5a, 6, 7, 8, 9, 9a, 10a-octahydro-2-methyl-4-oxo-4a, 7, 9-tris[ (trimethylsilyl)oxy]-4H-pyrano[2, 3-b][1,4]benzodioxin-6, 8-diyl]bis[methyl-, bis(phenylmethyl) ester, [4aS-(4aα, 5aα, 6α, 7α, 8α, 9β, 9aβ, 10aα)]-carbamic acid The enol ether, (22.0 g) [4a, 5a, 6, 7, 8, 9, 9a, 10a-octahydro-2-methyl-4, 4a, 7, 9 -tetrakis[(trimethylsilyl)oxyl]-2H-pyrano[2, 3-b] [ 1, 4]benzodioxin-6, 8-diyl]bis-[methyl-,bis(phenylmethyl) ester, [2R-(2α, 4aβ, 5aβ, 6β, 7β, 8β, 9α, 9aα, 10aβ)] -carbamic acid (38.4 g) of Formula IV was dissolved in CH₂Cl₂ (110 mL) and CuCl₂ dihydrate was added. The solution was stirred magnetically in a 1 neck round bottom flask with reflux condenser and nitrogen inlet. To 70% aqueous t-butyl hydroperoxide (5.00 mL) was added CH₂Cl₂ (5.0 mL) and the phases separated. The lower organic phase (containing t-butyl hydroperoxide and some water) was added to the enol ether solution and the mixture heated under reflux until the reaction was complete (about 4–5 hours). After cooling to 23°–25° C. solid sodium bisulfite (0.5 g) was added to quench any excess peroxide. Heptane (110 mL) was added and the mixture concentrated to half volume under reduced pressure. The solution was washed with water (100 mL) and then concentrated to a solid under reduced pressure to yield the title compound 19.6 g, 97% chemical yield.

I claim:

1. A process for preparing an alpha, beta-unsaturated enone of Formula I

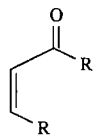   I which comprises oxidizing a silyl enol ether of Formula II

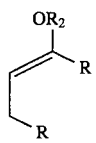   II with a radical intermediate generated by metal catalyst decomposition of a peroxide in the presence of a halogenated solvent or acetonitrile, at a temperature of −10° to 60° C., and where said metal catalyst is selected from the group of metal salts consisting of cuprous, cupric, manganese, nickel, cesium and chromium or hydrates thereof wherein R is selected from the group consisting of $(C_1-C_8)$ alkyl, phenyl, and substituted phenyl; $R_2$ is selected from the group consisting of triethylsilyl, trimethylsiyl, triphenylsilyl and diphenylmethylsilyl; and where the ratio of said peroxide to enol ether is 0.01 to 3 equivalents peroxide to 1 equivalent enol ether with the proviso that the peroxide used cannot be hydrogen peroxide.

2. A process according to claim 1 wherein the peroxide contains 0 to 70% water.

3. A process according to claim 1 wherein the catalyst is selected from the group consisting of cuprous chloride dihydrate and cupric chloride.

4. A process according to claim 3 wherein the catalyst is cupric chloride dihydrate.

* * * * *